(12) United States Patent
De Bodinat et al.

(10) Patent No.: US 7,947,743 B2
(45) Date of Patent: *May 24, 2011

(54) USE OF AGOMELATINE IN OBTAINING MEDICAMENTS INTENDED FOR THE TREATMENT OF BIPOLAR DISORDERS

(75) Inventors: Christian De Bodinat, Saint-Cloud (FR); Elisabeth Mocaer, Neuilly-sur-Seine (FR)

(73) Assignee: Les Laboratories Servier, Suresnes Cedex (FR)

( * ) Notice: Subject to any disclaimer, the term of this patent is extended or adjusted under 35 U.S.C. 154(b) by 1341 days.

This patent is subject to a terminal disclaimer.

(21) Appl. No.: 11/142,612

(22) Filed: Jun. 1, 2005

(65) Prior Publication Data

US 2006/0240127 A1  Oct. 26, 2006

(30) Foreign Application Priority Data

Apr. 20, 2005 (FR) ..................................... 05 03937

(51) Int. Cl.
*A61K 33/00* (2006.01)
*A61K 31/19* (2006.01)
*A61K 31/165* (2006.01)
*A61P 25/24* (2006.01)

(52) U.S. Cl. ........ 514/682; 514/617; 514/622; 514/557; 514/507; 514/510; 514/643; 514/646; 514/650; 514/658

(58) Field of Classification Search .................. 514/622, 514/557, 507, 510, 617, 643, 646, 650, 658, 514/682

See application file for complete search history.

(56) References Cited

U.S. PATENT DOCUMENTS

| 5,585,118 A * | 12/1996 | Stoll .............................. 424/488 |
| 7,122,576 B2 * | 10/2006 | Plata-Salaman et al. ...... 514/483 |
| 2006/0205754 A1* | 9/2006 | Willigers ...................... 514/288 |

OTHER PUBLICATIONS

Chilman-Blair, "Agomelatine: antidepressant treatment of bipolar disorder melatonin agonist/5-HT2C antagonist", Drugs of the Future, 2003, 28(1), pp. 7-13.*
Alda, "Pharmacogenetics of lithium response in bipolar disorder", Pharmacogenetics, 1999, 24(2), pp. 154-158.*
Goldberg, J.F., *Current Psychiatry*, 2010, 9 (5), 41-49.

* cited by examiner

*Primary Examiner* — Sreeni Padmanabhan
*Assistant Examiner* — Sahar Javanmard
(74) *Attorney, Agent, or Firm* — Hueschen and Sage

(57) ABSTRACT

The present invention relates to the use of agomelatine, or N-[2-(7-methoxy-1-naphthyl)ethyl]acetamide, on its own or in association, in obtaining medicaments intended for the treatment of bipolar disorders, especially bipolar disorders of types I and II, and more especially bipolar disorders of type I.

2 Claims, No Drawings

USE OF AGOMELATINE IN OBTAINING MEDICAMENTS INTENDED FOR THE TREATMENT OF BIPOLAR DISORDERS

The present invention relates to the use of agomelatine, or N-[2-(7-methoxy-1-naphthyl)ethyl]acetamide of formula (I):

on its own or in association, in obtaining medicaments intended for the treatment of bipolar disorders, especially bipolar disorders of types I and II, and more especially bipolar disorders of type I.

Agomelatine, or N-[2-(7-methoxy-1-naphthyl)ethyl]acetamide, has the double characteristic of being, on the one hand, an agonist of receptors of the melatoninergic system and, on the other hand, an antagonist of the $5\text{-HT}_{2C}$ receptor. These properties provide it with activity in the central nervous system and, more especially, in the treatment of major depression, seasonal affective disorder, sleep disorders, cardiovascular pathologies, pathologies of the digestive system, insomnia and fatigue due to jet-lag, appetite disorders and obesity.

Agomelatine, its preparation and its use in therapeutics have been described in European Patent Specification EP 0 447 285.

The Applicant has now found that agomelatine, or N-[2-(7-methoxy-1-naphthyl)ethyl]-acetamide, used on its own or in association, has valuable properties allowing its use in the treatment of bipolar disorders, especially bipolar disorders of types I and II, and more especially in bipolar disorders of type I.

Bipolar disorders are a psychopathological condition having a very severe impact on the life of patients, both on the social and family level and on the professional level. They are characterised by the generally repeated occurrence of depressive, manic, hypomanic or mixed episodes separated by periods during which the patients are a priori unaffected by major psychological dysfunction. In other words, patients suffering from bipolar disorders are marked by a vulnerability to marked fluctuations in mood in recurrent manner. The characteristics of the attacks and their development over time allow several clinical forms to be distinguised: type I bipolar disorder is the most typical and is characterised by one or more manic or mixed episodes usually accompanied by major depressive episodes; for its part, type II bipolar disorder involves the association of at least one major depressive episode and an episode of hypomania, a moderated form of mania. The risk of suicide in bipolar patients is very high, 25 to 50% of them having made at least one suicide attempt.

There is currently no satisfactory, recognised treatment for bipolar disorders. First-line treatments are usually mood stabilisers or thymoregulators but these treatments are often unable to relieve the depressive symptoms (J. Clin. Psychiatry, 2004, 65(4), 569-579). The concomitant prescription of an antidepressant, although frequently used, is a highly controversial practice because antidepressants may trigger or aggravate manic states and mixed states and must be stopped when a manic episode occurs.

Antidepressants are especially reputed to promote the causation or acceleration of hyperthymnic cycles and to promote, by two to three times, the occurrence of a manic or hypomanic course, and finally their prolonged use seems to lead to an increase in the number of depressive and manic episodes.

The Applicant has now found, surprisingly, that agomelatine can be used, on its own or in association, in the treatment of bipolar disorders, especially bipolar disorders of types I and HI, and more especially in bipolar disorders of type I.

Because of the very fact of its activity in depression, the effects that were to be expected in using agomelatine in bipolar disorders, and more especially in bipolar disorders of type I, were the same as the effects of the antidepressants described in the literature such as, for example, paroxetine.

Surprisingly, agomelatine does not behave like a conventional antidepressant, as has been observed in the course of a clinical study carried out in patients suffering from type I bipolar disorders. These results make it possible to consider its use, even its prolonged use, in bipolar disorders, especially bipolar disorders of types I and II, and more especially in bipolar disorders of type I.

The invention accordingly relates to the use of agomelatine, on its own or in association, in obtaining pharmaceutical compositions intended for the treatment of bipolar disorders, especially bipolar disorders of types I and II, and more especially bipolar disorders of type I.

The invention relates also to the association between agomelatine and a mood stabiliser or thymoregulatory agent for obtaining pharmaceutical compositions intended for the treatment of bipolar disorders, especially bipolar disorders of types I and II, and more especially bipolar disorders of type I.

The mood stabilisers or thymoregulatory agents according to the invention relate to lithium and antiepileptics such as, for example, carbamazepine, valproate and lamotrigine etc. More especially, the mood stabiliser or thymoregulatory agent of the association according to the invention will be lithium or valproate.

The pharmaceutical compositions will be presented in forms suitable for administration by the oral, parenteral, transcutaneous, nasal, rectal or perlingual route, and especially in the form of injectable preparations, tablets, sublingual tablets, glossettes, gelatin capsules, capsules, lozenges, suppositories, creams, ointments, dermal gels etc.

Besides agomelatine and the mood stabiliser optionally associated therewith, the pharmaceutical compositions according to the invention comprise one or more excipients or carriers selected from diluents, lubricants, binders, disintegration agents, absorbents, colourants, sweeteners etc.

By way of non-limiting example there may be mentioned:
- as diluents: lactose, dextrose, sucrose, mannitol, sorbitol, cellulose, glycerol,
- as lubricants: silica, talc, stearic acid and its magnesium and calcium salts, polyethylene glycol,
- as binders: aluminium and magnesium silicate, starch, gelatin, tragacanth, methylcellulose, sodium carboxymethylcellulose and polyvinylpyrrolidone,
- as disintegrants: agar, alginic acid and its sodium salt, effervescent mixtures.

The useful dosage varies according to the sex, age and weight of the patient, the administration route, the nature of the disorder and any associated treatments and ranges from 1 mg to 50 mg of agomelatine per 24 hours.

The daily dose of agomelatine will preferably be 25 mg per day.

Pharmaceutical Composition:

Formula for the preparation of 1000 tablets each containing 25 mg of active ingredient:

| | |
|---|---|
| N-[2-(7-methoxy-1-naphthyl)ethyl]acetamide | 25 g |
| Lactose monohydrate | 62 g |
| Magnesium stearate | 1.3 g |
| Povidone | 9 g |
| Anhydrous colloidal silica | 0.3 g |
| Cellulose sodium glycolate | 30 g |
| Stearic acid | 2.6 g |

Clinical Study:

This study was carried out in 21 patients suffering from bipolar disorders of type I, treated for at least 6 months with lithium (n=14) or valproate (n=7). Treatment for 6 weeks with agomelatine (25 mg/day) was carried out. Of these patients, 19 continued treatment beyond the 6 weeks of acute treatment, and 11 of those continued treatment up to 1 year. The results obtained showed that 81% of patients responded positively to the treatment—about 50% by the end of just one week of treatment. At the end of the one year treatment period, 10 out of the 11 patients were in remission. Only three manic or hypomanic episodes were observed after the 6 weeks of treatment, a level entirely compatible with those encountered with a mood stabiliser, clearly demonstrating that the positive action of agomelatine in type I bipolar patients is not associated with an increase in the incidence of manic and/or hypomanic episodes even over a long period of treatment.

The invention claimed is:

1. A method for treating a living animal body, including a human, afflicted with bipolar disorders of type I, comprising the step of administering to the living animal body, including a human, an amount of agomelatine, or N-[2-(7-methoxy-1-naphthyl)ethyl]acetamide, which is effective for alleviation of bipolar disorders of type I.

2. A method for treating a living animal body, including a human, afflicted with bipolar disorders of type I, comprising the step of administering to the living animal body, including a human, an amount of a composition comprising a combination of agomelatine and a thymoregulatory agent selected from lithium and valproate which is effective for alleviation of bipolar disorders of type I.

* * * * *

UNITED STATES PATENT AND TRADEMARK OFFICE
CERTIFICATE OF CORRECTION

| | | |
|---|---|---|
| PATENT NO. | : 7,947,743 B2 | |
| APPLICATION NO. | : 11/142612 | |
| DATED | : May 24, 2011 | |
| INVENTOR(S) | : Christian De Bodinat et al. | |

It is certified that error appears in the above-identified patent and that said Letters Patent is hereby corrected as shown below:

Title Page, item (73); Assignee: "Les Laboratories Servier" should be --Les Laboratoires Servier--.

Signed and Sealed this
Second Day of August, 2011

David J. Kappos
*Director of the United States Patent and Trademark Office*